US010227647B2

(12) United States Patent
Ke et al.

(10) Patent No.: US 10,227,647 B2
(45) Date of Patent: Mar. 12, 2019

(54) DNA SEQUENCING USING CONTROLLED STRAND DISPLACEMENT

(71) Applicant: Complete Genomics, Inc., Mountain View, CA (US)

(72) Inventors: Rongqin Ke, Mountain View, CA (US); Snezana Drmanac, Los Altos Hills, CA (US); Radoje Drmanac, Los Altos Hills, CA (US); Guangyang Cai, Milpitas, CA (US); Matthew Callow, Redwood City, CA (US)

(73) Assignee: Complete Genomics, Inc., San Jose, CA (US)

( * ) Notice: Subject to any disclaimer, the term of this patent is extended or adjusted under 35 U.S.C. 154(b) by 172 days.

(21) Appl. No.: 15/040,906

(22) Filed: Feb. 10, 2016

(65) Prior Publication Data
US 2016/0237488 A1    Aug. 18, 2016

Related U.S. Application Data

(60) Provisional application No. 62/194,741, filed on Jul. 20, 2015, provisional application No. 62/117,391, filed on Feb. 17, 2015.

(51) Int. Cl.
*C12Q 1/68* (2018.01)
*C12Q 1/6874* (2018.01)
*C12Q 1/6806* (2018.01)

(52) U.S. Cl.
CPC ......... *C12Q 1/6874* (2013.01); *C12Q 1/6806* (2013.01)

(58) Field of Classification Search
CPC ................ C12Q 1/6806; C12Q 1/6874; C12Q 2525/191; C12Q 2531/119
See application file for complete search history.

(56) References Cited

U.S. PATENT DOCUMENTS

| | | | |
|---|---|---|---|
| 5,270,184 | A | 12/1993 | Walker et al. |
| 6,210,891 | B1 | 4/2001 | Nyren et al. |
| 6,787,308 | B2 | 9/2004 | Balasubramanian et al. |
| 6,828,100 | B1 | 12/2004 | Ronaghi |
| 6,833,246 | B2 | 12/2004 | Balasubramanian |
| 6,897,023 | B2 | 5/2005 | Fu et al. |
| 6,911,345 | B2 | 6/2005 | Quake et al. |
| 6,969,488 | B2 | 11/2005 | Bridgham et al. |
| 7,897,344 | B2 | 3/2011 | Dahl et al. |
| 8,206,913 | B1 | 6/2012 | Kamberov et al. |
| 8,445,194 | B2 | 5/2013 | Drmanac et al. |
| 8,592,150 | B2 | 11/2013 | Drmanac et al. |
| 8,609,335 | B2 | 12/2013 | Drmanac et al. |
| 2003/0022207 | A1 | 1/2003 | Balasubramanian et al. |
| 2003/0064398 | A1 | 4/2003 | Barnes |
| 2004/0106130 | A1 | 6/2004 | Besemer et al. |
| 2004/0185484 | A1 | 9/2004 | Costa et al. |
| 2008/0003571 | A1 | 1/2008 | Mckernan et al. |
| 2010/0120098 | A1 | 5/2010 | Grunenwald et al. |
| 2011/0281738 | A1 | 11/2011 | Drmanac et al. |
| 2012/0004126 | A1 | 1/2012 | Drmanac et al. |
| 2012/0115145 | A1 | 5/2012 | Fu |
| 2012/0156728 | A1 | 6/2012 | Li et al. |
| 2014/0213461 | A1 | 7/2014 | Drmanac et al. |

FOREIGN PATENT DOCUMENTS

| | | |
|---|---|---|
| CN | 107250383 | 10/2017 |
| EP | 3259372 | 12/2017 |
| WO | 1999/019341 A1 | 8/1998 |
| WO | 1998/044151 A1 | 10/1998 |
| WO | 2000/018957 A1 | 4/2000 |
| WO | 2005/065814 A1 | 7/2005 |
| WO | 2005/082098 A1 | 9/2005 |
| WO | 2006/073504 A2 | 7/2006 |

OTHER PUBLICATIONS

Adessi, C., et al., "Solid phase DNA amplicfication: characterisation of primer attachment and amplification mechanisms" Nucleic Acids Res. 28, e87 (2000).
Bentley, et al., 2008, Nature, 456(7218): 53-59, Nov. 2008.
Brenner, S., et al., "Gene expression analysis by massively parallel signature sequencing (MPSS) on microbead arrays" Nat. Biotechnol. 18, 630-634 (2000).
Drmanac, R., et al., "Accurate Whole Genome Sequencing as the Ultimate Genetic Test." Clinical Chemistry 61.1 (2015): 305-306.
Drmanac, R., et al., "Human genome sequencing using unchained base reads on self-assembling DNA nanoarrays." Science 327.5961 (2010): 78-81.
Drmanac, S., et al., "Accurate sequencing by hybridization for DNA diagnostics and individual genomics." Nat. Biotechnol. 16, 54-58 (1998).
Hommelsheim, et al., Scientific Reports 4:5052 (2014).
Margulies, et al., "Genome sequencing in microfabricated high-density picolitre reactors." Nature 437:7057 (2005).
Margulies, M., et al., "Genome sequencing in microfabricated high-density picolitre reactors." Nature 437.7057 (2005): 376-380.
Meng, H-M, et al., "DNA dendrimer: an efficient nanocarrier of functional nucleic acids for intracellular molecular sensing." ACS Nano 8.6 (2014): 6171-6181.
Metzker, Michael L. "Sequencing technologies—the next generation." Nature Reviews Genetics 11.1 (2010): 31-46.

(Continued)

*Primary Examiner* — David C Thomas
(74) *Attorney, Agent, or Firm* — Kilpatrick Townsend & Stockton LLP

(57) ABSTRACT

This application discloses methods of producing a DNA strand for sequencing, as well as genetic constructs, libraries, and arrays using DNA strands produced according to these methods. The application also discloses methods of sequencing using the DNA strands, genetic constructs, libraries, and arrays produced. In certain aspects, DNA being sequenced includes a target sequence and at least one adaptor sequence.

17 Claims, 6 Drawing Sheets

Specification includes a Sequence Listing.

(56) References Cited

OTHER PUBLICATIONS

Ng, S., et al., "Targeted capture and massively parallel sequencing of 12 human exomes." Nature 461.7261 (2009) 272-276.
Ronaghi, et al., "Real-time DNA sequencing using detection of pyrophosphate release" Anal. Biochem. 242, 84-89 (1996).
Shendure, J. and H. Ji. "Next-generation DNA Sequencing." Nature Biotechnology 26.10 (2008): 1135-1145.
Shendure, J., et al., "Advanced sequencing technologies: methods and goals". Nat. Rev. Genet. 5, 335-344 (2004).
Shendure, J., et al., Accurate multiplex polony sequencing of an evolved bacterial genome. Science 309, 1728-1732 (2005).
International Preliminary Report on Patentability received in International Patent Application No. PCT/US2016/017390, filed Feb. 10, 2016. dated Aug. 31, 2017. 9 pages.
Extended European Search Report received in European Patent Application No. 16752821.5, dated Oct. 5, 2018. 9 pages.

Adaptor: Ad 141-2

DNB Primers: used to synthesize second strand

Ad120_3T_21bp: 5' GAT CGG GCT TCG ACT GGA GAC 3'

CX117: 5' AAG TCG GAG GCC AAG 3'

Complement Strand Primers: used to perform SBS on second Strand

AD041_5T_Complement: 5' AGA CCG CTT GGC CTC CGA CTT 3'

AD041_Helper: 5' AGC TCG AGC TTG TCT TCC TA 3'

SEQUENCE LISTING

<160> NUMBER OF SEQ ID NOS: 6

<210> SEQ ID NO 1
<211> LENGTH: 67
<212> TYPE: DNA
<213> ORGANISM: Artificial Sequence
<220> FEATURE:
<223> OTHER INFORMATION: synthetic nucleotide sequence (Ad 141-2)

<400> SEQUENCE: 1
aagtcggagg ccaagcggtc ttaggaagac aagctcgagc tcgagcgatc gggcttcgac    60
tggagac                                                              67

<210> SEQ ID NO 2
<211> LENGTH: 21
<212> TYPE: DNA
<213> ORGANISM: Artificial Sequence
<220> FEATURE:
<223> OTHER INFORMATION: synthetic first extension primer
      (Ad120_3T_21bp)

<400> SEQUENCE: 2
gatcgggctt cgactggaga c                                              21

<210> SEQ ID NO 3

```
<211> LENGTH: 15
<212> TYPE: DNA
<213> ORGANISM: Artificial Sequence
<220> FEATURE:
<223> OTHER INFORMATION: synthetic second extension primer (CX117)

<400> SEQUENCE: 3
aagtcggagg ccaag                                                    15

<210> SEQ ID NO 4
<211> LENGTH: 67
<212> TYPE: DNA
<213> ORGANISM: Artificial Sequence
<220> FEATURE:
<223> OTHER INFORMATION: synthetic nucleotide (complement of Ad 141-2)

<400> SEQUENCE: 4
gtctccagtc gaagcccgat cgctcgagct cgagcttgtc ttcctaagac cgcttggcct   60
ccgactt                                                             67

<210> SEQ ID NO 5
<211> LENGTH: 21
<212> TYPE: DNA
<213> ORGANISM: Artificial Sequence
<220> FEATURE:
<223> OTHER INFORMATION: synthetic complement strand primer
      (AD041_5T_Complement)

<400> SEQUENCE: 5
agaccgcttg gcctccgact t                                             21

<210> SEQ ID NO 6
<211> LENGTH: 20
<212> TYPE: DNA
<213> ORGANISM: Artificial Sequence
<220> FEATURE:
<223> OTHER INFORMATION: synthetic complement strand primer
      (AD041_Helper)

<400> SEQUENCE: 6
agctcgagct tgtcttccta                                               20
```

DNA SEQUENCING USING CONTROLLED STRAND DISPLACEMENT

CROSS-REFERENCES TO RELATED APPLICATIONS

This application claims priority to U.S. Provisional Application Nos. 62/117,391 (filed Feb. 17, 2015) and 62/194,741 (filed Jul. 20, 2015). The entire content of each of the aforementioned provisional applications is incorporated herein by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file SequenceListing_092171-0969248.txt, created Apr. 21, 2016, 1,815 bytes, machine format IBM-PC, MS-Windows operating system, is hereby incorporated by reference.

FIELD OF THE INVENTION

This invention relates to the fields of DNA sequencing, genomics, and molecular biology.

BACKGROUND

The need for low cost, high-throughput, methods for nucleic acid sequencing and re-sequencing has led to the development "massively parallel sequencing" (MPS) technologies. Improvements in such sequencing methods are of great value in science, medicine and agriculture.

BRIEF SUMMARY OF INVENTION

The present invention is related to nucleic acid sequencing (e.g., genomic DNA sequencing). In one aspect, methods of paired-end sequencing of single stranded DNAs, such as DNA concatemers (e.g., DNA nanoballs or DNBs) are provided. Typically DNA being sequenced includes a target sequence and at least one adaptor sequence.

The invention provides a method of producing a DNA strand complementary to a template DNA polynucleotide immobilized on a substrate, said template DNA comprising a first target DNA sequence interposed between a first adaptor 3' to the first target DNA sequence. The method comprises hybridizing a first primer to a first primer binding sequence in the first adaptor; extending the first primer using a first DNA polymerase to generate a second strand, which comprises a sequence complementary to the first target DNA sequence and a sequence complementary to at least part of the second adaptor; hybridizing a second primer to a second primer binding sequence; and extending the second primer using a DNA polymerase having strand-displacement activity to generate a third strand. Said third strand partially displaces said second strand and produces a partially hybridized second strand, comprising: 1) a hybridized portion that is hybridized to the template DNA polynucleotide; and 2) an unhybridized overhang portion that contains a sequence that is complementary to the first target DNA sequence and a sequence that is complementary to at least part of the second adaptor.

In some embodiments, the DNA template polynucleotide comprises an additional adaptor, i.e., a third adaptor, which is 3' to the first adaptor; and an additional target DNA sequence, i.e., a second target DNA sequence, interposed between the first adaptor and the third adaptor. In one embodiment, the template DNA polynucleotide comprises a third adaptor and the second primer binding sequence is in the third adaptor. In another embodiment, the second primer binding sequence is in the first adaptor, the same adaptor that also comprises the first primer.

In one embodiment, the first DNA polymerase—used to generate the second strand—and the DNA polymerase having strand-displacement activity—used to generate the third strand—are the same polymerase. In one embodiment, the first primer and the second primer are hybridized to their respective primer binding sequences or extended in the same reaction.

In one embodiment, the method further comprises hybridizing a sequencing oligonucleotide to the sequence that is complementary to at least part of the second adaptor, and determining the nucleotide sequence of at least part of the sequence complementary to the first target DNA sequence.

In one embodiment, the first adaptor, the second adaptor, and the third adaptor if present, have the same nucleotide sequence.

In one embodiment, the template DNA polynucleotide comprises a DNA concatemer, and the first target DNA sequence and the second target DNA sequence have the same nucleotide sequence.

In one embodiment, the template DNA polynucleotide comprises a DNA concatemer and the first primer and the second primer have the same nucleotide sequence.

In one embodiment, a plurality of third strands are produced by hybridizing a plurality of second primers comprising extendable and non-extendable primers to a plurality of second primer binding sequences.

In one embodiment, the extension of the second primer to generate the third strand is terminated at a fixed time interval of 5 min, 10 min, 20 min, 30 min, 40 min or 60 min. In one embodiment, the termination is achieved by a chemical termination, i.e., by adding chemicals. In one embodiment, the chemical used to terminate the reaction is a Tris buffer containing 1.5 M NaCl. In another embodiment, the termination is achieved by incorporation of chain terminating nucleotide analogs, such as ddNTPs. In some embodiments, ddNTPs are added after addition of a chemical termination agent.

In one embodiment, the reaction of extending the second primer is controlled by selecting temperature, enzyme concentration, and primer concentration such that the complement displacement of the second strand can be avoided.

DETAILED DESCRIPTION OF THE INVENTION

1. Overview

In certain first aspects, the invention provides methods of producing a DNA strand for sequencing, as well as genetic constructs, libraries, and arrays using DNA strands produced according to these methods. In certain second aspects, the invention provides methods of sequencing using DNA strands, genetic constructs, libraries, and arrays produced according to the first aspects.

Producing a DNA Strand for Sequencing

In one approach, a DNA strand for sequencing is produced by:

a) providing a template DNA polynucleotide comprising a first target DNA sequence interposed between a first adaptor 3' to the first target DNA sequence and a second adaptor 5' to the first target DNA sequence, and optionally comprising a third adaptor 3' to the first adaptor and a second target DNA sequence interposed between the first adaptor and the third adaptor, wherein the template DNA polynucleotide is immobilized on a substrate, b) combining a first primer with the immobilized template DNA polynucleotide, and hybridizing the first primer to a first primer binding sequence in the first adaptor, wherein the first primer is not immobilized on the substrate when it is combined with the immobilized template DNA polynucleotide;

c) extending the first primer using a first DNA polymerase to generate a second strand, wherein the second strand comprises a sequence complementary to the first target DNA sequence and a sequence complementary to at least part of the second adaptor;

d) combining a second primer with the immobilized template DNA polynucleotide, hybridizing a second primer to a second primer binding sequence, wherein the second primer binding sequence is 3' to the first primer binding sequence, wherein the second primer is not immobilized on the substrate when it is combined with the immobilized template DNA polynucleotide;

e) extending the second primer using a DNA polymerase having strand-displacement activity to generate a third strand, wherein extending the second primer to generate the third strand partially displaces the second strand, thereby producing a partially hybridized second strand having:

(i) a hybridized portion that is hybridized to the template DNA polynucleotide, and (ii) an unhybridized overhang portion that contains a sequence that is complementary to the first target DNA sequence and a sequence that is complementary to at least part of the second adaptor, wherein the unhybridized portion is 3' in the second strand to the hybridized portion.

Figure 1:
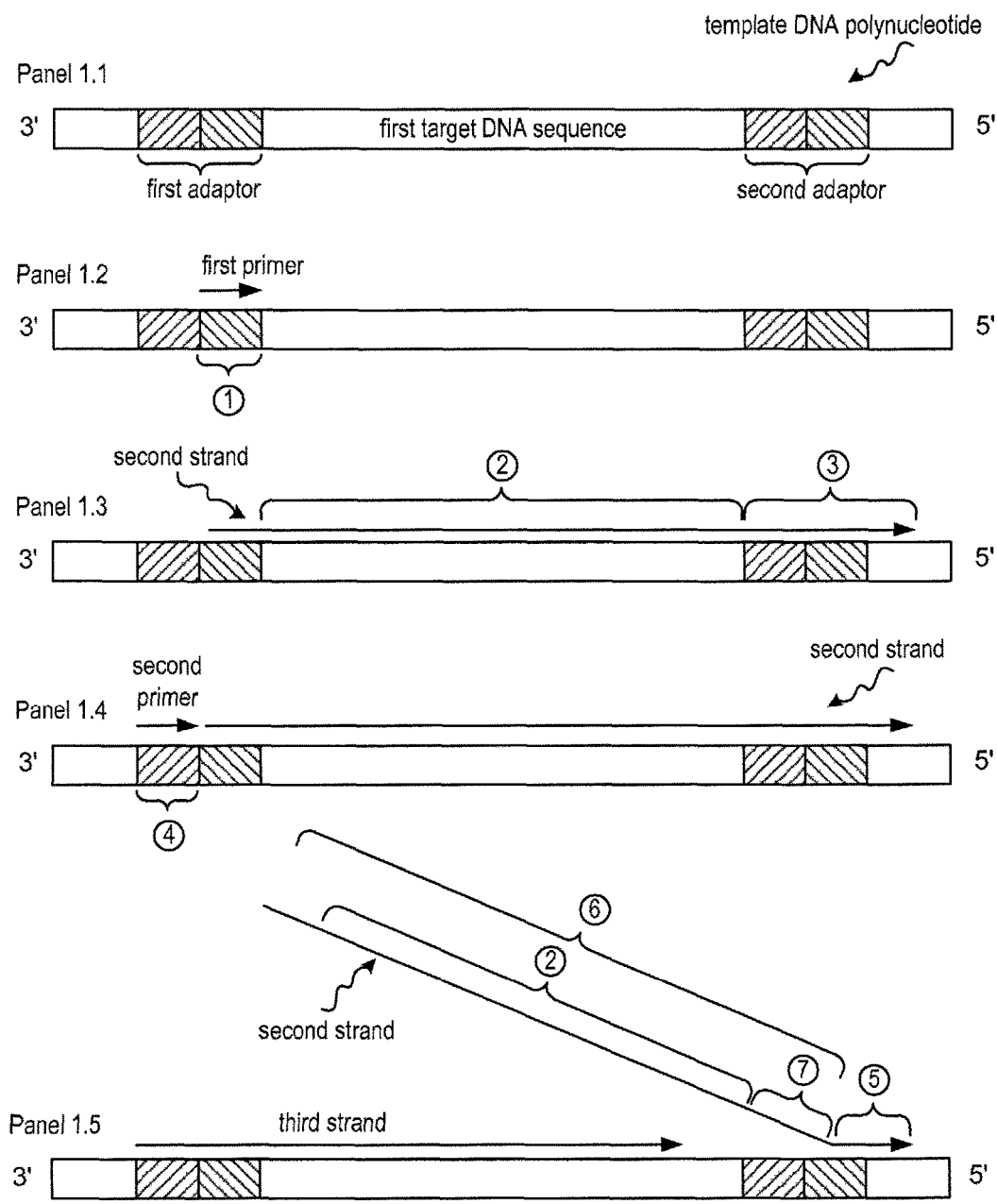
FIG. 1 illustrates steps used in a method for producing a DNA strand for sequencing.

FIG. 1 illustrates steps (a)-(e) above.

Panel 1.1 shows a template DNA polynucleotide comprising a first target DNA sequence interposed between a first adaptor 3' to the first target DNA sequence and a second adaptor 5' to the first target DNA sequence.

Panel 1.2 shows a first primer hybridized to a first primer binding sequence ① in the first adaptor.

Panel 1.3 shows the first primer is extended using a first DNA polymerase to generate a second strand, wherein the second strand comprises a (i) sequence complementary to the first target DNA sequence ② and a (ii) sequence complementary to at least part of the second adaptor ③.

Panel 1.4 shows hybridizing a second primer to a second primer binding sequence ④, wherein the second primer binding sequence is 3' to the first primer binding sequence. In the example shown in FIG. 1, the second primer binding sequence is contained in the first adaptor 3' (to the first primer binding sequence). (Compare to FIG. 2, Panel 2.4, in which the second primer binding sequence is in a third adaptor.)

Panel 1.5 shows extending the second primer using a DNA polymerase having strand-displacement activity to generate a third strand. As shown in Panel 1.5. the extension of the third strand partially displaces the second strand. This partial displacement results in a second strand that is partially hybridized to the template DNA polynucleotide (or "first strand"). The partially hybridized second strand has a hybridized portion ⑤ that is hybridized to the template DNA polynucleotide, and an unhybridized overhang portion ⑥ that contains a sequence that is complementary to the first target DNA sequence ② and a sequence that is complementary to at least part of the second adaptor ⑦.

Figure 2:
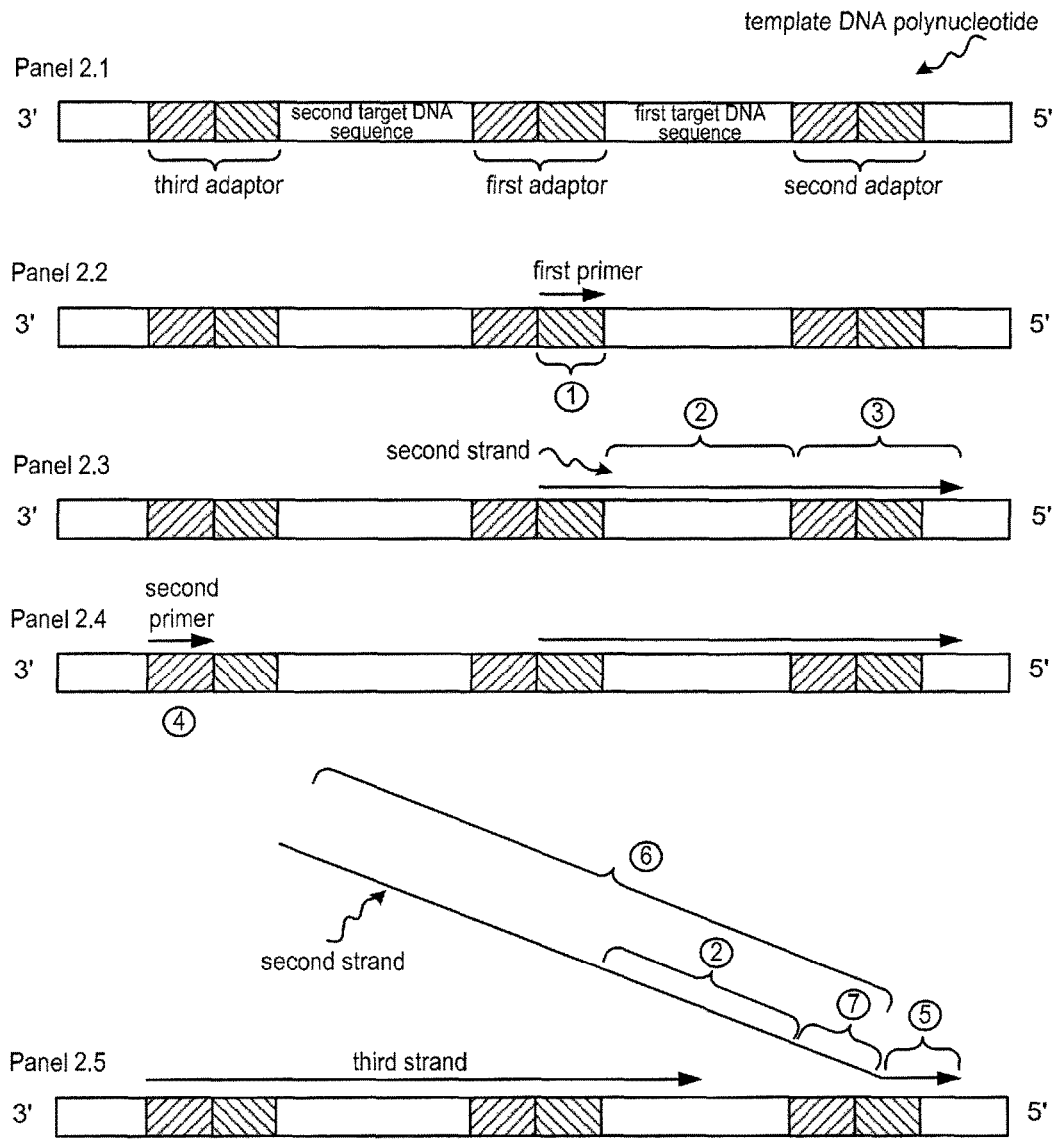
FIG. 2 illustrates steps used in a related method for producing a DNA strand for sequencing.

FIG. 2 shows a second scheme to illustrate steps (a)-(e) above.

Panel 2.1 shows a template DNA polynucleotide comprising (i) a first target DNA sequence interposed between a first adaptor 3' to the first target DNA sequence and a second adaptor 5' to the first target DNA sequence and (ii) a third adaptor 3' to the first adaptor and a second target DNA sequence interposed between the first adaptor and the third adaptor.

Panel 2.2 shows a first primer hybridized to a first primer binding sequence ① in the first adaptor.

Panel 2.3 shows the first primer is extended using a first DNA polymerase to generate a second strand, wherein the second strand comprises a (i) sequence complementary to the first target DNA sequence ② and a (ii) sequence complementary to at least part of the second adaptor ③.

Panel 2.4 shows hybridizing a second primer to a second primer binding sequence ④, where the second primer binding sequence is 3' to the first primer binding sequence. As shown in FIG. 2, the second primer binding sequence is contained in the third adaptor.

Panel 2.5 shows extending the second primer using a DNA polymerase having strand-displacement activity to generate a third strand. As shown in Panel 2.5, the extension of the third strand partially displaces the second strand. This partial displacement results in a second strand that is partially hybridized to the template DNA polynucleotide (or "first strand"). The partially hybridized second strand has a hybridized portion ⑤ that is hybridized to the template DNA polynucleotide, and an unhybridized overhang portion ⑥ that contains a sequence that is complementary to the first target DNA sequence ② and a sequence that is complementary to at least part of the second adaptor ⑦.

Sequencing a DNA Strand

DNA sequencing methods may be applied using the partially hybridized second strand as a sequencing template. Because the second strand comprises a sequence complementary to the first target DNA sequence, this method may be used to determine the nucleotide sequence of the first target DNA sequence.

In one approach, the sequencing step comprises:

f) hybridizing a sequencing oligonucleotide to the sequence in the third strand that is complementary to at least part of the second adaptor, and g) determining at least part of the sequence that is complementary to the first target DNA sequence. The process of sequence determining may include, for example and not limitation, sequencing by synthesis (comprising extending the sequencing oligonucleotide) and/or sequencing by ligation (comprising ligating a probe to the sequencing oligonucleotide), or may include other methods.

Figure 3:
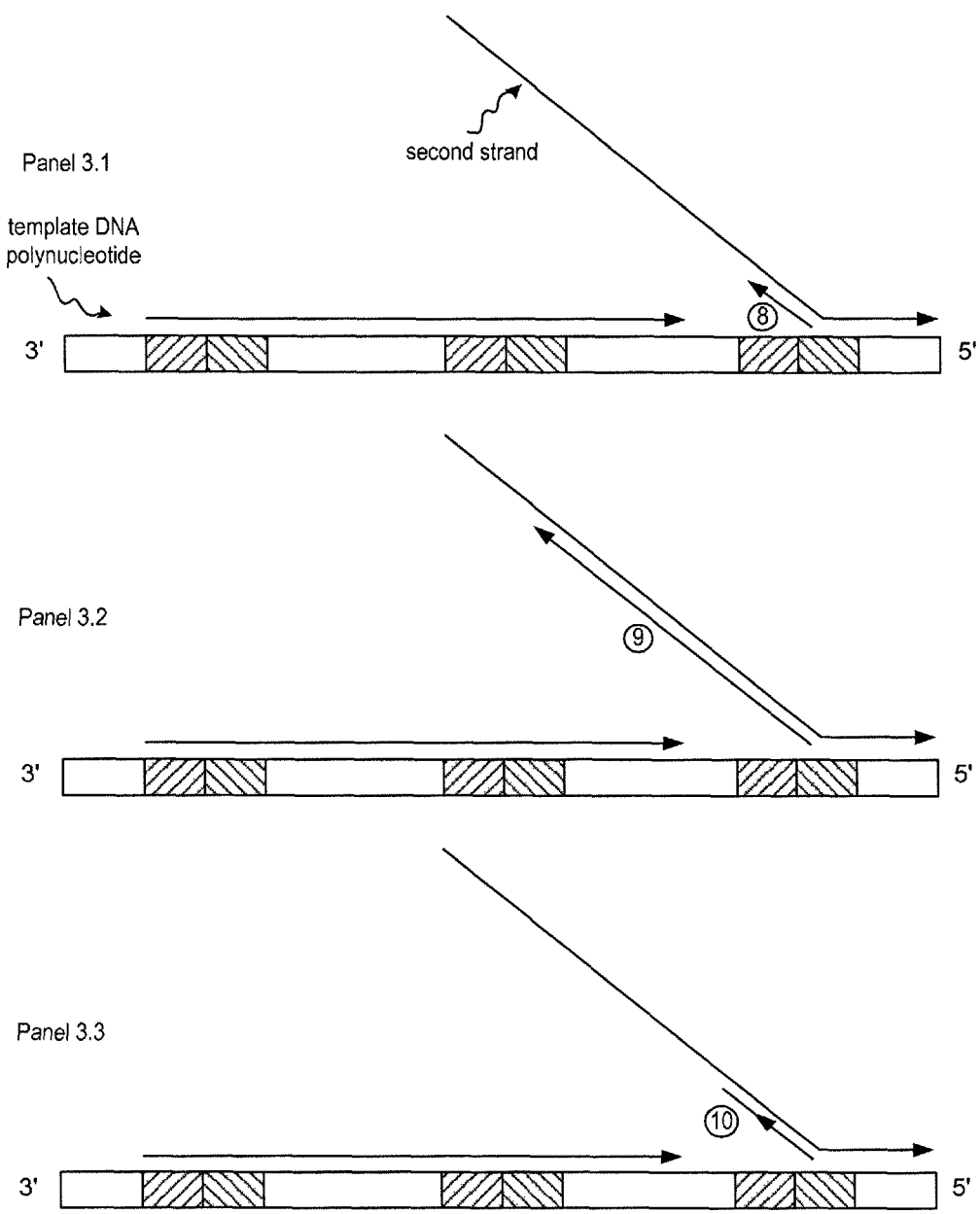
FIG. 3 illustrates steps used in determining sequence from a DNA strand.

FIG. 3 shows a scheme to illustrate steps (f)-(g) above.

Panel 3.1 shows hybridizing a sequencing oligonucleotide ⑧ to a sequence in the second strand that is complementary to at least part of the second adaptor.

Panel 3.2 shows extending the sequencing oligonucleotide to determine least part of the sequence that is complementary to the first target DNA sequence (and thereby determining the first target sequence) using sequencing by synthesis methods in which the sequencing oligonucleotide acts as a primer for primer extension to produce extension product ⑨.

Panel 3.3 shows ligating a probe ⑩ to the sequencing oligonucleotide, thereby producing a ligation product comprising sequence complementary to the second strand sequence, thereby determining sequence of the second strand (and thereby determining the first target sequence) using a sequencing by ligation method.

Each of these elements and steps is described in more detail. It will be appreciated that although aspects of the present invention is described with reference to specific embodiments or illustrations, other embodiments will be apparent to those skilled in the art upon reading the present disclosure, and such other embodiments are contemplated to be within the present inventive methods.

2. Template DNA Polynucleotide

As used in this description, a "template DNA polynucleotide" is a DNA construct that comprises a target DNA sequence interposed between two adaptor sequences, referred to herein as a "first adaptor," 3' to the target DNA sequence and a "second adaptor," 5' to the target DNA sequence. As used herein, "interposed" means the target DNA sequence is between the adaptor sequences. In some embodiments, the target DNA sequence is contiguous with the adaptor sequences and no other bases or sequences are present (e.g., present between the target DNA sequence and adaptor sequence(s)) but this is not required in all embodiments. A sequence that is interposed between adaptors may also be referred to as a sequence flanked by adaptors.

Using the methods of the invention, at least a part of the target DNA sequence is determined. Target DNAs may be from any number of sources, as described below.

The template DNA polynucleotide may be generated using any methods for associating a target DNA sequence(s) of interest with flanking adaptors. For example, a target DNA sequence of interest may be obtained from a biological source, such as a cell, tissue, organism or population of cells or organisms, and flanking adaptors may be added by ligation, amplification, transposition, insertion, etc. See, e.g., U.S. Pat. No. 8,445,194 (describing DNA nanoballs comprising adaptors and target sequences), International Patent Publication No. WO 00/18957 (describing sequencing target sequences flanked by adaptors), and U.S. Patent Publication No. US 2010/0120098 (describing fragmentation), each of which is incorporated in its entirety for all purposes.

3. Libraries of Template DNA Polynucleotide

In many massively parallel sequencing (MPS) technologies, a library of sequencing templates is generated and individual species in the library are sequenced in parallel. For example, in the DNA nanoball approach developed by Drmanac et al., genomic DNA is fragmented, and individual fragments are used to produce circular DNAs in which platform-specific oligonucleotide adapters separate genomic DNA sequences (which separated genomic DNA sequences may be contiguous in the genome). The circular DNAs are amplified to generate single-stranded concatemers ("DNA nanoballs") which may be immobilized on a substrate. In "Solexa" type sequencing, genomic DNA is fragmented and the DNA fragments are then ligated to platform-specific oligonucleotide adapters. The adaptors are used to immobilize individual fragments on a substrate where they are amplified in situ to produce clonally clustered amplicons for sequencing. Many other MPS sequencing approaches are known.

Thus, it will be recognized that, although, the present invention is sometimes described in terms of a target DNA (e.g., a single DNB template DNA), MPS sequencing is carried out using a large libraries of sequences, typically on arrays (e.g., arrays comprising DNA concatemers or clonal copies of the template DNA polynucleotides) of constructs comprising numerous different target sequences (e.g., different genomic DNA fragments) but sharing common adaptor sequences.

Method for making MPS sequencing libraries, and methods of sequencing using such libraries, are well known in the art, and familiarity by the reader with such methods is assumed. See, for example, Shendure, J. and H. Ji. "Next-generation DNA sequencing." *Nature biotechnology* 26.10 (2008): 1135-1145; Shendure, J., et al. "Advanced sequencing technologies: methods and goals". *Nat. Rev. Genet.* 5, 335-344 (2004); Metzker, Michael L. "Sequencing technologies—the next generation." *Nature Reviews Genetics* 11.1 (2010): 31-46; Drmanac, R. et al. "Accurate Whole Genome Sequencing as the Ultimate Genetic Test." *Clinical Chemistry* 61.1 (2015): 305-306; Drmanac, R. et al. "Human genome sequencing using unchained base reads on self-assembling DNA nanoarrays." *Science* 327.5961 (2010): 78-81; Drmanac, S. et al. "Accurate sequencing by hybridization for DNA diagnostics and individual genomics." *Nat. Biotechnol.* 16, 54-58 (1998); Margulies, M. et al. "Genome sequencing in microfabricated high-density picoliter reactors." *Nature* 437.7057 (2005): 376-380; Ng, S. et al. "Targeted capture and massively parallel sequencing of 12 human exomes." *Nature* 461.7261 (2009): 272-276; Meng, H-M et al. "DNA dendrimer: an efficient nanocarrier of functional nucleic acids for intracellular molecular sensing." *ACS Nano* 8.6 (2014): 6171-6181; Head, S. et al. "Practical Guide"; Head, S. et al. "Practical Guide."; Shendure, J. et al. Accurate multiplex polony sequencing of an evolved bacterial genome. *Science* 309, 1728-1732 (2005); Brenner, S. et al. "Gene expression analysis by massively parallel signature sequencing (MPSS) on microbead arrays" *Nat. Biotechnol.* 18, 630-634 (2000); Ronaghi et al. "Real-time DNA sequencing using detection of pyrophosphate release" *Anal. Biochem.* 242, 84-89 (1996); McKernan, K. et al. "Reagents, methods, and libraries for bead-based sequencing," US patent application 20080003571 (2006); Adessi, C. et al. "Solid phase DNA amplification: characterisation of primer attachment and amplification mechanisms" *Nucleic Acids Res.* 28, e87 (2000), each of which is incorporated in its entirely for all purposes, including for teaching preparation of DNA sequencing libraries and MPS sequencing platforms and techniques.

4. Target DNA Sequence

The target DNA portion of the template DNA polynucleotide may be from any source, including naturally occurring sequences (such as genomic DNA, cDNA, mitochondrial DNA, cell free DNA, etc.), artificial sequences (e.g., synthetic sequences, products of gene shuffling or molecular evolution, etc.) or combinations thereof. Target DNA may be derived from sources such as an organism or cell (e.g., from plants, animals, viruses, bacteria, fungi, humans, mammals, insects), forensic sources, etc. Target DNA sequences may be from a population of organisms, such as a population of gut bacteria. A target DNA sequence may be obtained directly from a sample, or may be a product of an amplification reaction, a fragmentation reaction, and the like.

A target DNA may have a length within a particular size range, such as 50 to 600 nucleotides in length. Other exemplary size ranges include 25 to 2000, 50 to 1000, 100 to 600, 50-100, 50-300, 100-300, and 100-400 nucleotides in length. In a template DNA polynucleotide having two or more different target DNAs, the target DNAs may be the same length or different lengths. In a library of a template DNA polynucleotide, the members of the library may have, in some embodiments, similar lengths (e.g., all in the range of 25 to 2000 nucleotides, or another range).

In one approach, target DNAs may be prepared by fragmenting a larger source DNA (e.g., genomic DNA) to produce fragments in a desired size range. In some approaches a size-selection step is used to obtain a pool of fragments within a particular size range.

5. Adaptors

A template DNA, or template DNA polynucleotide, as used in the methods disclosure herein, includes two or more adaptors. Adaptors may comprise elements for immobilizing template DNA polynucleotides on a substrate, elements for binding oligonucleotides used in sequence determination (e.g., binding sites for primers extended in sequencing by synthesis methods and/or probes for cPAL or other ligation based sequencing methods, and the like), or both elements for immobilization and sequencing. Adaptors may include additional features such as, without limitation, restriction endonuclease recognition sites, extension primer hybridization sites (for use in analysis), bar code sequences, unique molecular identifier sequences, and polymerase recognition sequences.

Adaptor sequences may have a length, structure, and other properties appropriate for a particular sequencing platform and intended use. For example, adaptors may be single-stranded, double-stranded, or partially-double stranded, and may be of a length suitable for the intended use. For example, adaptors may have length in the range of 10-200 nucleotides, 20-100 nucleotides, 40-100 nucleotides, or 50-80 nucleotides. In some embodiments, an adaptor may comprise one or more modified nucleotides that contain modifications to the base, sugar, and/or phosphate moieties.

It will be appreciated by the skilled reader that different members of a library will typically contain common adaptor sequences, although different species or subgenera in the library may have unique features such as sub-genera-specific bar codes.

An individual adaptor sequence may include multiple functionally distinct subsequences. For example, as discussed in detail in this disclosure, a single adaptor sequence may contain two more primer binding sequences (which can be recognized by different complementary primers or probes). Functionally distinct sequences within an adaptor may be overlapping or non-overlapping. For illustration, given a 40-base long adaptor, in one embodiment, bases 1-20 are a first primer binding site and bases 21-40 are a second primer binding site. In a different embodiment, bases 1-15 are a first primer binding site and bases 21-40 are a second primer binding site. In a different embodiment, bases 5-25 are a first primer binding site and bases 15-35 are a second primer binding site. Likewise, given a 40-base long adaptor, bases 1-20 can be an immobilization sequence and bases 21-40 can be a primer binding site. Different primer binding sequences in an adaptor (or in different adaptors of a template DNA polynucleotide, may have the same or different lengths.

Adaptors (e.g., first adaptors, second adaptors, third adaptor, etc.) may comprise one, two or more than two primer binding sequences. A primer binding sequence is defined functionally as the site or sequence to which a primer (or oligonucleotide) specifically binds. For example, an adaptor with two primer binding sequences may be specifically bound by two different primers. In one approach the two primer binding sequences in the same adaptor are overlapping, i.e., sharing part of the nucleotide sequence. In some embodiments, the overlapped region is no more than 50%, or 40%, or 30%, or 20%, or 10% or 5% of either of the two overlapping primer binding sequences. In one approach the more than one primer binding sequences are non-overlapping. In some embodiments, the non-overlapping primer binding sequences are immediately adjacent to each other; in some other embodiments, the non-overlapping primer binding sequences are separate by 1-10, 10-20, 30-40, or 40-50 nucleotides.

Primer binding sequences will be of sufficient length to allow hybridization of a primer, with the precise length and sequence dependent on the intended functions of the primer (e.g., extension primer, ligation substrate, indexing sequence, etc.). Primer binding sequences are often at least 10, at least 12, at least 15 or at least 18 bases in length.

It will be apparent that within a given template DNA polynucleotide, different adaptors may have the same sequence or different sequences, and may have the same primer binding sequences, or different primer binding sequences. See, e.g., Sec. 7 below. Although certain drawings are provided to illustrate the invention, representations of adaptors using similar cross-hatching and the like should not be constructed as indicating identity of sequences.

6. Primers

The terms "primers" and "probes" may be used interchangeably and refer to oligonucleotides having a sequence complementary to a primer or probe binding site of a DNA. These primers may be "extension primers" or "sequencing oligonucleotides." "Extension primers" are used in primer extension reactions to generate the "second" and "third" [DNA] strands described above. Thus, an extension primer is a substrate for a DNA polymerase that is extendible by addition of nucleotides.

It will be well within the ability of one of ordinary skill in the art to select or design primers and probes for use in the present invention (e.g., primers capable of extension or ligation under sequencing assay conditions). Without intending to limit the invention, extension primers often have a length in the range of 10-100 nucleotides, often 12-80 nucleotides, and often 15-80 nucleotides.

It will be appreciated that primers and probes may be fully or partially complementary to the binding sequence in an adaptor to which it hybridizes. For example, a primer may have at least 85%, 90%, 95%, or 100% identity to the sequence to which it hybridizes.

A primer may also contain additional sequence at the 5' end of the primer that is not complementary to the primer binding sequence in the adaptor. The non-complementary portion of a primer may be at a length that does not interfere with the hybridization between the primer and its primer binding sequence. In general, the non-complementary portion is 1 to 100 nucleotides long. In some embodiments, the non-complementary portion is 4 to 8 nucleotides long. Primers may comprise DNA and/or RNA moieties, and in some approaches primers used in the invention may have also one or more modified nucleotides that contain modifications to the base, sugar, and/or phosphate moieties.

A "sequencing oligonucleotide" may be an extension primer used in sequencing-by-synthesis reactions (also called "sequencing by extension"). A "sequencing oligonucleotide" may be an oligonucleotide used in a sequencing-by-ligation method such as "combinatorial probe-anchor ligation reaction" (cPAL) (including single, double and multiple cPAL) as described in US Patent Publication 20140213461, incorporated herein by reference for all purposes. In brief, cPAL comprises cycling of the following steps: First, a "sequencing oligonucleotide" (or "anchor") is hybridized to a complementary sequence in an adaptor of the third DNA strand described above. Enzymatic ligation reactions are then performed with the anchor to a fully degenerate probe population of, e.g., 8-mer probes that are labeled, e.g., with fluorescent dyes. Probes may comprise, e.g., about 6 to about 20 bases in length, to about 7 to about 12 bases in length. At any given cycle, the population of 8-mer probes that is used is structured such that the identity of one or more of its positions is correlated with the identity of the fluorophore attached to that, e.g., 8-mer probe. In variations of basic cPAL well known in the art, such as multiple cPAL, partially or fully degenerate secondary anchors are used to increase the readable sequence.

7. Relationships of Target Sequences and Adaptor Sequences

As noted above, a template DNA polynucleotide comprises a first target DNA sequence interposed between a first adaptor 3' to the first target DNA sequence and a second adaptor 5' to the first target DNA sequence.

The template DNA polynucleotide may comprise a multiple target DNA sequences (e.g., more than 25 or more than 50; sometimes in the range of 2 to 1000, 50-800, or 300-600 copies), each of which may be flanked by a pair of adaptors. Thus, in one embodiment, a template DNA polynucleotide comprises a third adaptor 3' to the first adaptor and a second target DNA sequence interposed between the first adaptor and the third adaptor. In some cases, target DNA sequences are contained in a single-stranded DNA nanoball. For example see Section 7.1 and FIGS. 2 and 4.

The template DNA polynucleotide may comprise a single target DNA sequence flanked by two adaptors (sometimes called "an adaptored target sequence"). For example see Section 7.2 and FIGS. 1 and 6.

7.1. Template DNA Polynucleotides: Concatemers and DNBs

In some embodiments, a template DNA polynucleotide used in the invention is a DNA concatemer. As used in this context, the term "concatemer" refers to a long continuous DNA molecule that contains multiple copies of the same DNA sequences (the "monomer" or "monomeric sequence" linked in series). A "DNA concatemer" may comprise at least two, at least three, at least four, at least 10, at least 25 monomers, at least 50 monomers, at least 200 monomers, or at least 500 monomers. In some embodiments, the DNA concatemer comprises 25-1000 monomers, such as 50-800 monomers or 300-600 monomers). Each monomer comprises at least one target DNA sequence. A DNA concatemer used in the methods of the invention may be a DNA nanoball, or "DNB." Without intending to limit the present invention in any fashion, DNA nanoballs are described in Drmanac et al., 2010, "Human genome sequencing using unchained base reads on self-assembling DNA nanoarrays." *Science* 327:5961:78-81; Dahl et al. "Methods and oligonucleotide designs for insertion of multiple adaptors into library constructs." U.S. Pat. No. 7,897,344 (Mar. 1, 2011); Drmanac et al. "Single Molecule Arrays for Genetic and Chemical Analysis" U.S. Pat. No. 8,445,194 (May 21, 2013); and Drmanac et al. "Methods and compositions for long fragment read sequencing" U.S. Pat. No. 8,592,150 (Nov. 26, 2013), each of which is incorporated herein by reference, and other references described herein. "DNA nanoballs" or "DNBs" are single-stranded DNA concatemers of sufficient length to form random coils that fill a roughly spherical volume in solution (e.g., SSC buffer at room temperature). In some embodiments, DNA nanoballs typically have a diameter of from about 100 to 300 nm. A template DNA that is in a DNB may be referred to as a "DNB template strand."

In one embodiment, monomer of the concatemer comprise one adaptor sequence and one target DNA sequence. Because monomers are linked in series, target DNA sequences will be flanked by two adaptor sequences.

In some approaches, the target DNA sequence in the monomer is flanked by two "half-adaptor" sequences, such that each target sequence linked in series in the concatemer is flanked by two adaptors.

In some approaches, the monomeric unit comprises one, two, three, or four, or more adaptors. In some embodiments, all of adaptors of a monomer (and concatemer) have the same sequence. On other embodiments, adaptors may have different sequences, such as two, three or four different sequences.

It will be recognized that individual monomers may comprise more than one template DNA sequence. For example, a monomer may comprise the structure $A_1$-$T_1$-$A_2$-$T_2$ where $T_1$ and $T_2$ are template DNAs with the same or different sequences, and $A_1$ and $A_2$ are adaptors with the same or different sequence. The corresponding concatemer will have the structure $A_1$-$T_1$-$A_2$-$T_2$-$A_1$-$T_1$-$A_2$-$T_2$-$A_1$-$T_1$-$A_2$-$T_2$ . . . . In a related embodiment, the a monomer may comprise the structure $A_1$-$T_1$-$A_2$-$T_2$-$A_3$ where $T_1$ and $T_2$ are template DNAs with the same or different sequences, $A_2$ is an adaptor and $A_1$ and $A_3$ are "half adaptors." The corresponding concatemer will include the structure $A_2$-$T_2$-$A_3$ $A_1$-$T_1$-$A_2$-$T_2$-$A_3$ $A_1$-$T_1$-$A_2$-$T_2$-$A_3$ $A_1$ . . . where the $A_3$ $A_1$ half adaptors together function as an adaptor. For illustration and not limitation, TABLE 1 illustrates exemplary concatemer structures. In TABLE 1, N is greater than 1. Usually N is at least 3, often at least 4, at least 10, at least 25 monomers, at least 50 monomers, at least 200 monomers, or at least 500 monomers. In some embodiments, N is in the range of 25-1000, such as 50-800, or 300-600. In cases in which the template DNA polynucleotide is a DNA nanoball, N is at least 25, usually at least 50, and often in the range 50-800, or 300-600.

TABLE 1

Concatemer Structures

| [Mononner]$_N$ | T = target sequence(s), A = adaptor sequence(s); N > 1 (e.g., N = 2-10, e.g., 2-5) |
|---|---|
| 1 [A$_1$-T$_1$]$_N$ | Concatemer includes A$_1$-T$_1$-A$_1$-T$_1$-A$_1$ |
| 2 [A$_1$-T$_1$-A$_1$]$_N$ | A$_1$ may be a 'half' adaptor Concatemer includes A$_1$ A$_1$-T$_1$-A$_1$ A$_1$-T$_1$-A$_1$ A$_1$-T$_1$-A$_1$ A$_1$ |
| 3 [A$_1$-T$_1$-A$_2$-T$_1$]$_N$ | A$_1$ and A$_2$ may be the same or different; Concatemer includes A$_1$-T$_1$-A$_2$-T$_1$-A$_1$-T$_1$-A$_2$-T$_1$-A$_1$-T$_1$-A$_2$-T$_1$ |
| 4 [A$_1$-T$_1$-A$_2$]$_N$ | A$_1$ and A$_2$ may be the same or different; A$_1$ and A$_2$ may be a 'half' adaptors Concatemer includes A$_2$ A$_1$-T$_1$-A$_2$ A$_1$-T$_1$-A$_2$ A$_1$ |
| 5 [A$_1$-T$_1$-A$_1$-T$_2$]$_N$ | T$_1$ and T$_2$ may be the same or different. Concatemer includes A$_1$-T$_1$-A$_1$-T$_2$-A$_1$-T$_1$-A$_1$-T$_2$-A$_1$-T$_1$-A$_1$ |
| 6 [A$_1$-T$_1$-A$_2$-T$_1$]$_N$ | A$_1$ and A$_2$ may be the same or different. concatemer includes A$_1$-T$_1$-A$_2$-T$_1$-A$_1$-T$_1$-A$_2$-T$_1$-A$_1$-T$_1$-A$_2$ |
| 7 [A$_1$-T$_1$-A$_2$-T$_2$-A$_3$-T$_3$]$_N$ | T$_1$, T$_2$, and T$_3$ independently may be the same or different. A$_1$, A$_2$, and A$_3$ independently may be the same or different. Concatemer includes A$_1$-T$_1$-A$_2$-T$_2$-A$_3$-T$_3$-A$_1$-T$_1$-A$_2$-T$_2$-A$_3$-T$_3$ |

DNA concatemers (including DNA nanoballs), can be produced by any suitable method. In one approach, a single genomic fragment is used to generate a single-stranded circular DNA with adaptors interspersed between target sequences that are contiguous or close together in the genome. The circular DNA construct may be amplified enzymatically, e.g., by rolling circle replication, or by ligation of monomers to each other. For illustration and not limitation, DNA nanoballs may be prepared according to the methods described in U.S. Pat. No. 8,445,194 and U.S. Pat. No. 8,592,150.

7.2 Template DNA Polynucleotides: Adaptored Target Sequences

Alternatively, the template DNA polynucleotide may comprise a single target DNA sequence flanked by two adaptors. Template DNA polynucleotides with a single target DNA sequences and a pair of flanking adaptors may be of particular use in Solexa-type sequencing. See, e.g., FIG. 6.

In some embodiments, the template DNA is a non-concatemeric DNA construct that comprises at least one target DNA sequence and at least two adaptors. In some embodiments the construct comprises more than two adaptors and/or more than one target DNA sequence.

In some embodiments, a complementary strand is first synthesized from a single DNA strand comprising one or more adaptors and one or more target DNA sequences to form a double stranded DNA. One or both of the two strands of the double stranded DNA can be used as the template DNA.

In some embodiments, clonal copies of the non-concatemer are produced and used as template DNAs in accordance with the invention. Methods of producing clonal copies of a DNA sequence, including a non-concatemer, are well known in the art. See references cited in Section 3, above.

8. Substrates and Compartments

In some applications, template DNA polynucleotides are immobilized on a substrate. Generally, the immobilization occurs prior to synthesis of the "second" and "third" strands discussed above. In some cases the immobilization occurs prior to synthesis of the "third" strands discussed above. Exemplary substrates may be substantially planar (e.g., slides) or nonplanar and unitary or formed from a plurality of distinct units (e.g., beads). Exemplary materials include glass, ceramic, silica, silicon, metal, elastomer (e.g., silicone), polyacrylamide (e.g., a polyacrylamide hydrogel; see WO 2005/065814). In some embodiments, the substrate comprises an ordered or non-ordered array of immobilization sites or wells. In some approaches, target DNA polynucleotides are immobilized on a substantially planar substrate, such as a substrate comprising an ordered or non-ordered array of immobilization sites or wells. In some approaches, target DNA polynucleotides are immobilized on beads.

Polynucleotides can be immobilized on a substrate by a variety of techniques, including covalent and non-covalent attachment. Polynucleotides can be fixed to a substrate by a variety of techniques. In one embodiment, a surface may include capture probes that form complexes, e.g., double stranded duplexes, with component of the polynucleotide molecule, such as an adaptor oligonucleotide. In another embodiment, a surface may have reactive functionalities that react with complementary functionalities on the polynucleotide molecules to form a covalent linkage. Long DNA molecules, e.g., several nucleotides or larger, may also be efficiently attached to hydrophobic surfaces, such as a clean glass surface that has a low concentration of various reactive functionalities, such as —OH groups. In still another embodiment, polynucleotide molecules can be adsorbed to a surface through non-specific interactions with the surface, or through non-covalent interactions such as hydrogen bonding, van der Waals forces, and the like.

For example, a DNA nanoball may be immobilized to a discrete spaced apart region as described in U.S. Pat. No. 8,609,335 to Drmanac et al. In one approach adaptored DNAs are immobilized on a substrate by hybridization to immobilized probe sequences, and solid-phase nucleic acid amplification methods are used to produce clonal clusters comprising DNA template polynucleotides. See, e.g., WO 98/44151 and WO 00/18957.

In some embodiments, DNA template polynucleotides are compartmentalized in an emulsion, droplets, on beads and/or in microwells (Margulies et al. "Genome sequencing in microfabricated high-density picoliter reactors." *Nature* 437:7057 (2005); Shendure et al. "Accurate multiplex polony sequencing of an evolved bacterial genome" *Science* 309, 1728-1732 (2005) prior to the primer extension steps.

9. DNA Polymerases

The methods of the present invention may be carried out using methods, tools and reagents well known to those of ordinary skill in the art of molecular biology and MPS sequencing, including nucleic acid polymerases (RNA polymerase, DNA polymerase, reverse transcriptase), phosphatases and phosphorylases, DNA ligases, and the like. In particular, certain primer extension steps may be carried out using one or more DNA polymerases. Certain extension steps are carried out using DNA polymerase with strand displacement activity.

The methods disclosed herein use the polymerase and strand displacement activities of DNA polymerase to generate DNA strands complementary to a template DNA. In one approach, the present invention uses a DNA polymerase with a strong 5'→3' strand displacement activity. Preferably the polymerase does not have 5'→3' exonuclease activity. However, DNA polymerases having 5'-3' exonuclease activity may be used when the activity does not prevent the implementation of the method of the invention, e.g., by using reaction conditions that inhibit the exonuclease activity.

The term "strand displacement activity" describes the ability to displace downstream DNA encountered during synthesis. Strand displacement activity is described in US Pat. Pub. No. 20120115145, incorporated herein by reference, as follows: "Strand displacement activity" designates the phenomenon by which a biological, chemical or physical agent, for example a DNA polymerase, causes the dissociation of a paired nucleic acid from its complementary strand in a direction from 5 towards 3, in conjunction with, and close to, the template-dependent nucleic acid synthesis. The strand displacement starts at the 5' end of a paired nucleic acid sequence and the enzyme therefore carries out the nucleic acid synthesis immediately in 5' of the displacement site. The neosynthesized nucleic acid and the displaced nucleic acid generally have the same nucleotide sequence, which is complementary to the template nucleic acid strand. The strand displacement activity may be situated on the same molecule as that conferring the activity of nucleic acid synthesis, and particularly the DNA synthesis, or it may be a separate and independent activity. DNA polymerases such as E. coli DNA polymerase I, Klenow fragment of DNA polymerase I, T7 or T5 bacteriophage DNA polymerase, and HIV virus reverse transcriptase are enzymes which possess both the polymerase activity and the strand displacement activity. Agents such as helicases can be used in conjunction with inducing agents which do not possess strand displacement activity in order to produce the strand displacement effect, that is to say the displacement of a nucleic acid coupled to the synthesis of a nucleic acid of the same sequence. Likewise, proteins such as Rec A or Single Strand Binding Protein from E. coli or from another organism could be used to produce or to promote the strand displacement, in conjunction with other inducing agents (Kornberg and Baker, 1992, DNA Replication, 2nd Edition, pp 113-225, Freeman, N.Y.).

In one approach, the polymerase is Phi29 polymerase. Phi29 polymerase has a strong displacement activity at moderate temperatures (e.g., 20-37° C.).

In one approach, Bst DNA Polymerase, Large Fragment (NEB #MO275) is used. Bst DNA Polymerase is active at elevated temperatures (~65° C.).

In one approach, the polymerase is Deep-VentR DNA polymerase (NEB #MO258) (Hommelsheim et al., *Scientific Reports* 4:5052 (2014)).

10. Producing Complementary Strands

This section describes certain aspects of the steps of producing second and third DNA strands.

Generation of DNA strands complementary to the template DNA or target DNA sequence ("the first strand"), starts with hybridizing a first primer to a first primer binding sequence in the first adaptor in the template DNA. See FIG. 1, Panel 1.2 and FIG. 2, Panel 2.2. The first primer is then extended by a first DNA polymerase to generate a second strand. See FIG. 1, Panel 1.3 and FIG. 2, Panel 2.3. The first DNA polymerase can be a polymerase having strand displacement activity or one not having strand displacement activity.

A third strand is generated by extending a second primer that is hybridized to a second primer binding sequence, 3' to the first primer binding sequence in the template DNA. The second primer binding sequence can be in a third adaptor, if present. See FIG. 2, Panel 2.4. The second primer binding sequence can also be in the same adaptor as the first primer binding sequence, and 3' to the first primer binding sequence. See FIG. 1, Panel 1.4. Extension of the second primer to produce the third strand is performed using a DNA polymerase having strand displacement activity. See FIG. 1, Panel 1.5 and FIG. 2, Panel 2.5. The third strand, during the extension process, displaces the 5' portion of the second strand it encounters and causes the second strand to partially dissociate from the template DNA and form an overhang. See FIG. 1, Panel 1.5 and FIG. 2, Panel 2.5.

The extension-displacement reaction is controlled such that the second strand, rather than being completely displaced, is partially hybridized to the template DNA and partially unhybridized. The unhybridized portion ("overhang") contains a first sequence that is complementary to the first target DNA sequence, a sequence that is complementary to at least a part of the first adaptor, and a third sequence that is complementary to at least part of the second adaptor, with the first sequence flanked by the second and third sequence. Thus, in one embodiment the overhang is flanked by adaptor sequences (or complements thereof), or portions thereof.

An example of a first target DNA sequence interposed between a first adaptor and a second adaptor is illustrated in FIG. 1. Another example of a first target DNA sequence interposed between a first adaptor and a second adaptor is illustrated in FIG. 2. The embodiment in FIG. 2 shows a second target DNA sequence interposed between the first adaptor and a third adaptor. In this case the first and second target DNA sequences may be the same, may be different, may be linked in the genome, etc., as discussed below.

In some embodiments, as illustrated in Items 3, 5, 6, and 7 of Table 1 and in FIG. 2, the template DNA comprises an additional adaptor (e.g., third adaptor), 3' to the first adaptor, and a second target DNA sequence interposed between the first adaptor and the third adaptor.

In this embodiment, the first adaptor comprises a first primer binding sequence that can bind a first primer; and the third adaptor comprises a second primer binding sequence that can bind a second primer. In some embodiments, the first target DNA and the second target DNA have the same nucleotide sequence. In some embodiments, the first target DNA and the second target DNA have different nucleotide sequence. The first, second, and third adaptors may have the same or different nucleotide sequence.

In one embodiment, as illustrated in FIG. 1, the first adaptor comprises both a first primer binding sequence that can bind a first primer, and a second primer binding sequence that can bind a second primer. The second primer binding sequence is 3' to the first primer binding sequence. The first and second adaptors may have the same or different nucleotide sequence. In one particular embodiment, the first and second adaptors have the same nucleotide sequence and each adaptor comprises two binding sequences for a first and second primers, respectively.

In some embodiments, the second adaptor in the template DNA comprises one or more primer binding sequences for one or more sequencing oligonucleotides. See FIG. 3.

10.1 Illustrative Example Using DNB Primers

Figure 4:
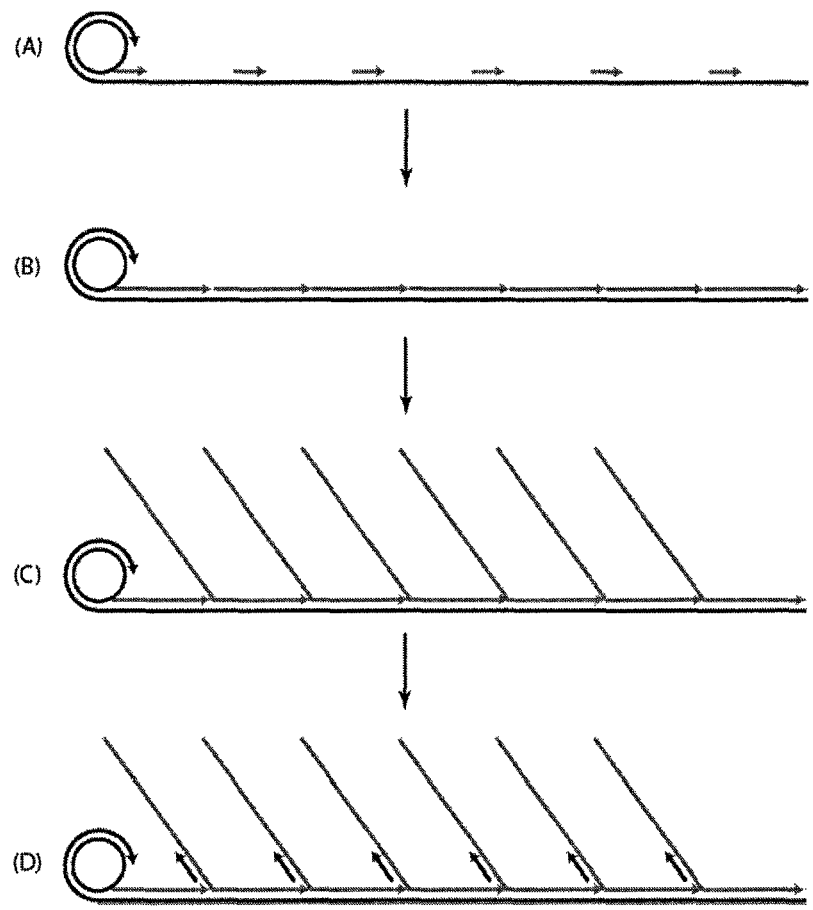
FIG. 4 illustrates an exemplary method of using an extension primer to generate the complementary strands (a series of follow-on fragments) on the DNBs using strand displacement activity of a DNA polymerase.

In one approach, the template DNA polynucleotide is a DNA concatemer, e.g., a DNB, comprising monomeric units of a DNA sequence having the structure illustrated in FIG. 1 or FIG. 2. FIG. 4 illustrates an example of generation of complementary strands from such a DNB. In this particular example, the template DNA polynucleotide may be DNB comprising monomeric units of a DNA structure as shown in FIG. 2, Panel 2.1. The DNB comprises a plurality of adaptors, all having the same nucleotide sequence. In (A), a DNB, each monomeric unit comprising an adaptor sequence and an inserted genomic DNA sequence, is hybridized with complementary primers. In one approach the primers are hybridized to the adaptor (e.g., to all or a portion of the adaptor sequences) on the template DNA strand. In (B), polymerization is performed to generate two or more of complementary strands, or follow-on fragments. In (C), when the 3' end of the newly synthesized strand (the third strand) reaches the 5' end of the downstream following strand (the second strand), the 5' portion of the following DNA strand (the second strand) is displaced by DNA polymerase, generating an overhang. One or more monomeric units of each concatemer may be displaced in this fashion.

The extension-displacement reaction conditions are controlled in order to generate second strands with total lengths and overhang lengths optimized for complementary strand sequencing. In one approach the reaction is terminated by incorporation of ddNTPs (or other means known to one of ordinary skill in the art) at a time determined to provide the desired product. See Section 12, below. In (D), after generating overhang fragments, a sequencing oligonucleotide can be hybridized (overhang) to the adaptor (i.e., the complement of the adaptor sequence of the template) in each overhang fragment. It will be recognized that, in one embodiment, the follow-on fragment comprises a overhang portion that is long enough to comprise at least one adaptor sequence, in addition to the adaptor sequence to which the extension primer binds, along with a hybridized (duplex) portion of sufficient length to keep the follow-on fragment annealed to the DNB template strand. This is followed by performing sequencing chemistry, which may be sequencing-by-synthesis (SBS) or other sequencing chemistries. The sequence generated will be the inserted (e.g., genomic) DNA adjacent to, and upstream, of the adaptor. This sequence information can be paired with sequence generated from sequencing the template strand. Typically sequencing the template strand provides sequence downstream of the adaptor.

Figure 5:
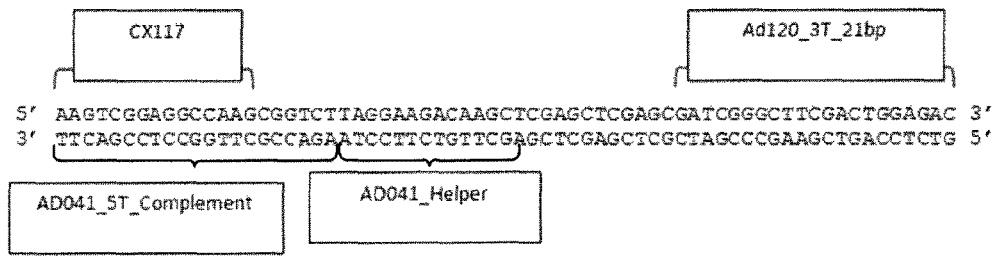
FIG. 5 shows exemplary adaptor and primer sequences for generation and sequencing of the DNA strands complementary to a DNB. (SEQ ID NOS:1 and 4=adaptor; SEQ ID NOS:2-3 and 5-6=primer)

FIG. 5 exemplifies primers that can be used to produce complementary strands according to the methods of the invention. Adaptor "Ad141-2" is ligated with genomic DNA fragments (not shown) and is used to produce single strand DNA circles. The produced DNA circles comprise the sequence of the top strand of an adapter "Ad 141-2" (shown in 5'-3' direction; SEQ ID NO:1) and the sequence of short target DNAs (e.g., genomic DNAs). DNBs are then produced from said DNA circles by rolling circle amplification. The DNBs so produced thus comprise the sequence of the bottom strand of "Ad 141-2" (shown in 3'-5' direction; SEQ ID NO:4) and can be used as the template DNA polynucleotide (first strand).

The adaptor comprising 67 bases has two primer binding sequences that bind CX117 (the second primer; SEQ ID NO:3) and AD120_3T_21b (the first primer; SEQ ID NO:2), respectively. CX117 and AD120_3T-21b are also referred to as DNB primers in FIG. 5. The extension of Ad120_3T produces a second strand and extension of the CX117 primer produces a third strand. The extension of the third strand displaces the second strand, which produced an overhang portion of the second strand, as discussed in section B. The Complement Strand Primers ("AD041_5T" and "AD041_Helper"; SEQ ID NOS:5-6)) are sequencing oligonucleotides, which can be used to perform sequencing by synthesis (SBS) on overhang portion of the second strand.

10.2 Producing Strands Complementary to an Adaptored DNA Fragment

In one approach, the template DNA polynucleotide is a non-concatemeric DNA (e.g., monomeric). A non-concatemeric DNA may have the structure as shown in FIG. 1, Panel 1.1.

Figure 6:
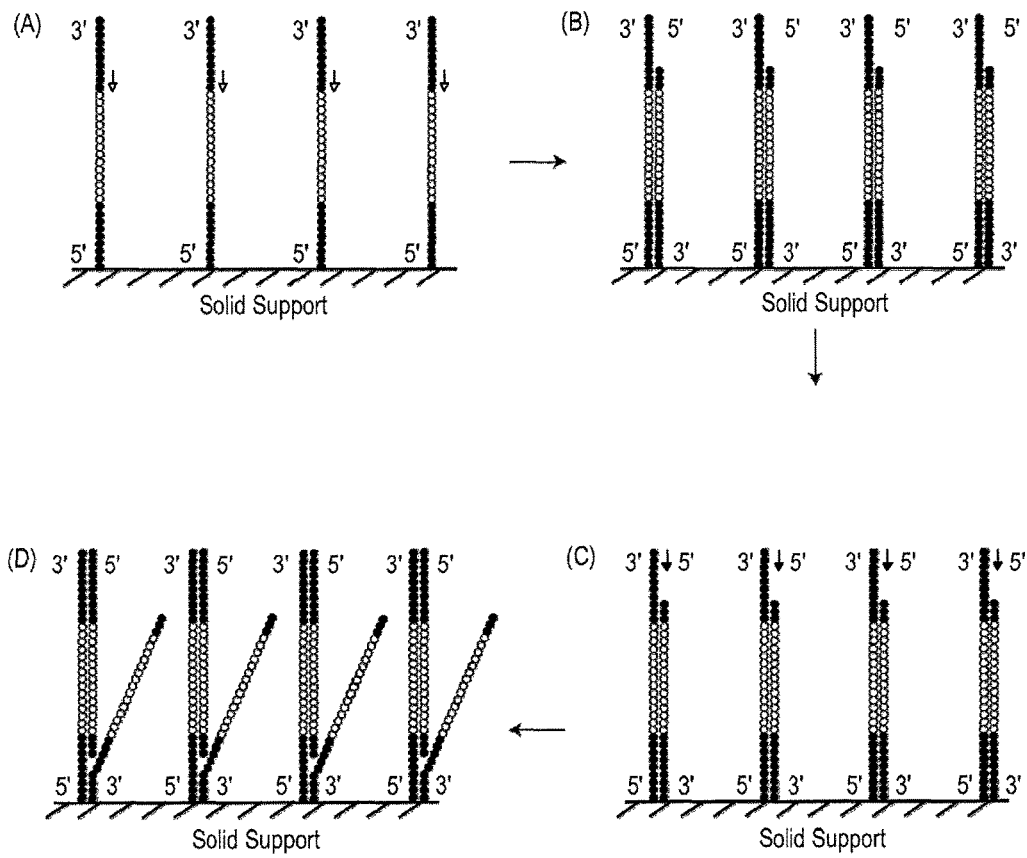
FIG. 6 is an illustration of an exemplary method for generation of DNA strands complementary to an immobilized adaptored DNA.

FIG. 6 illustrates one approach. In FIG. 6(A), four immobilized single stranded polynucleotides are shown. The open circles represent target sequences, and the filled circles represent 3' and 5' adaptor sequences (which may be the same or different). The four immobilized single stranded polynucleotides may be different or may be a cluster comprising clonal copies of the template DNA polynucleotide. An example is illustrated in FIG. 6, where clonal copies of single stranded monomeric DNAs (template DNAs) are immobilized on a substrate. Each template DNA comprises a target DNA is flanked by a first adaptor at the 5' and a second adaptor at 3'.

FIG. 6(A): A first primer (indicated by the arrow with open arrowhead) is hybridized to a first primer binding sequence on the first adaptor.

FIG. 6(B): The first primer is extended with a DNA polymerase to generate a second strand. The second strand so produced comprises a sequence that is complementary to the target DNA sequence and a sequence that is complementary to the second adaptor.

FIG. 6(C): A second primer (indicated by the arrow with filled arrow head) is hybridized to a second primer binding sequence that is 3' to the first primer binding sequence in the first adaptor. The second primer is extended to produce a third strand with a DNA polymerase having strand-displacement activity.

FIG. 6(D): The extension of the third strand is controlled such that the second strand is partially displaced, i.e., it remains attached to the template DNA through the hybridization to the second adaptor.

11. Order of Addition of Primers

The order of addition of the extension primers (e.g., first primer(s), second primer(s)) may vary. For example, in some embodiments a first primer and polymerase are added and synthesis of the second strand occurs (at least in part) prior to addition of the second primer. In another approach, the first and second primers are added at about the same time (see, e.g., Examples, below). For example, they may be added together in the same composition, or may be added separately within about 1 minute of each other, or within about 5 minutes of each other. The first and second extension primers may be added in any order.

Sequential addition of the primers may be necessary in approaches in which second strand is to be produced using a DNA polymerase that has no strand displacement activity, while the third strand is to be produced using a DNA polymerase having strand displacement activity.

It will be recognized that a single oligonucleotide may function as both an extension primer for producing the second strand and/or the third strand.

It will be further recognized that multiple different first primers and/or multiple different second primers and/or multiple different sequencing oligonucleotides may be used in the same sequencing reaction.

The sequencing oligonucleotide(s) for the second strand is typically added after the extension-displacement of the second strand is terminated using the methods disclosed herein. See the sections titled "Controlling the extension-displacement reaction to control; strand length and avoid complete displacement", infra.

The sequencing oligonucleotide hybridizes to the overhang portion of the second strand. In some embodiments, the sequencing oligonucleotide has a sequence that is complementary to and thus hybridizes to a known sequence within the first target sequence. In some embodiments, the sequencing oligonucleotide hybridizes to a sequence in the second strand that is complementary to at least part of the second adaptor. In some embodiments, the sequencing oligonucleotide is complementary, partially or completely, to the first or second primer.

12. Controlling the Extension-Displacement Reaction to Control; Strand Length and Avoid Complete Displacement To generate partially-displaced second strands (follow-on fragments) with both overhangs and duplex portions attached to the template DNA polynucleotide (e.g., DNB DNA strands), the extension reaction to produce the third strands may be controlled to avoid complete displacement of the second strands (i.e., "following strands" or "follow-on fragments") and to produce second and third strands having lengths suitable for sequencing. This can be achieved by controlling progression of the reaction by selecting a polymerase(s) with a suitable polymerization rate or other properties, and by using a variety of reaction parameters including (but not limited to) reaction temperature, duration of the reaction, primer composition, DNA polymerase, primer and dents concentration, additives and buffer composition. Optimal conditions may be determined empirically.

12.1 Choice of DNA Polymerase

One approach to control the extension-displacement reaction is to use a DNA polymerase having suitable strand displacement activities to produce the third strands. DNA polymerases having strand displacement activity include, but not limited to, Phi29, Bst DNA polymerase, Klenow fragment of DNA polymerase I, and Deep-VentR DNA polymerase (NEB#MO258). These DNA polymerases are known to have different strength of the strand displacement activity. See, Kornberg and Baker (1992, DNA Replication, Second Edition, pp. 113-225, Freeman, N.Y.). It is within one of ordinary skill in the art to select the DNA polymerase suitable for the invention.

12.2 Polymerase, Primer and dNTP Concentrations

Another approach to control the extension-displacement reaction is using suitable concentrations of the DNA polymerase having strand displacement activity, or dNTP, or the second primers.

12.3 Additives

In some embodiments, the extension reaction is controlled by including an agent that affects the duplex formation between extension primers and template DNA, such as DMSO (e.g., 1%-2%), Betaine (e.g., 0.5 M), glycerol (e.g., 10%-20%), T4 G32 SSB (e.g., 10-20 ng/ul), and volume exclusion agents, in the reaction buffer.

12.4 Temperature

The reaction temperatures may also be controlled to allow appropriate speed of polymerization and strand displacement. Higher temperature typically results in greater extent of strand displacement. In some embodiments, reaction temperatures are maintained to be within the range of 20° C.-37° C., for example, 32° C., 33° C., 34° C., 35° C., 36° C., or 37° C., in order to avoid complete displacement.

In some approaches, extension reactions are controlled by using a mixture of conventional (extendible) primers and non-extendible primers, i.e. 3' end blocked primers. A non-extendible primer blocks elongation via, for example, a chemical blocking group that prevents polymerization by a DNA polymerase. By mixing these two different primers at different ratios, the length of duplex (hybridized) portion of the newly synthesized complementary DNA strand (follow-on fragments) can be controlled. For example, in one approach a mixture of first primers is used in which 50-70% are non-extendible ("blocked") and 30-50% can be extended ("unblocked"). Many types of non-extendible primers are known in the art and would be suitable for the present invention.

12.5 Reaction Time

In some embodiments, the extension-displacement reaction is controlled by terminating the reaction after a certain period of time during which the desired length of the second strands is achieved. In some embodiments, the reaction is terminated after 5 min, 10 min, 20 min, 30 min, 40 min or 60 min from initiation. Methods of termination of the reaction are well known in the art, for example, by incorporation of ddNTPs or by adding chemical solutions, e.g., a Tris buffer containing 1.5 M NaCl. In one preferred embodiment, the termination is achieved by incorporating ddNTPs after adding to the reaction a Tris buffer containing 1.5M NaCl.

13. Sequence Determination

In some embodiments, the claimed invention provides methods of determining the sequence of the second strands produced as described above. The method comprises hybridizing a sequencing oligonucleotide to the sequence in the second strand that is complementary to at least part of the second adaptor (See FIG. 3, Panel 3.1), and determining the nucleotide sequence of at least part of the sequence complementary to the first target DNA sequence. Sequence determination may be carried out using sequencing-by-synthesis methods (FIG. 3, Panel 3.2) or using sequencing-by-ligation methods (FIG. 3, Panel 3.3), or both.

In one embodiment, the produced DNA strands complementary to the template DNA are used for sequence determination of the target DNA. Overhangs of the second strands are sequenced by extending primers hybridized to the complementary sequences of the second adaptor, for example, as illustrated FIG. 3.

In another embodiment, the template DNA strand is also sequenced using primers hybridized to the first adaptor. The sequence information from the complementary strands is paired with sequences generated from sequencing the template DNA to determine the entire target DNA sequence.

It will be apparent to the reader that variations of the specific embodiments outlined herein may be used. In one approach, the extension primers and sequencing oligonucleotides bind to different portions of an adaptor sequence. In one approach, the extension primers and sequencing oligonucleotides bind to the same portion of the adaptor sequence (e.g., a portion of the adaptor sequence for extension and the complement of same portion of the adaptor sequence for sequencing).

Any suitable sequence determination method may be used to determine the sequence of the overhang, for example, SBS, pyrosequencing, sequencing by ligation, and others. In some embodiments more than one sequencing approach is used. For example, the template DNA strand may be sequenced using one method (e.g., cPAL) and the third strands are sequenced using a different method (e.g., SBS).

Sequencing-by-synthesis (SBS) may rely on DNA polymerase activity to perform chain extension during the sequencing reaction step. SBS is well known in the art. See, e.g., U.S. Pat. Nos. 6,210,891; 6,828,100, 6,833,246; 6,911,345; 6,969,488; 6,897,023; 6,833,246; and 6,787,308; Patent Publication Nos. 200401061 30; 20030064398; and 20030022207; Margulies et al., 2005, *Nature* 437:376-380; Ronaghi et al., 1996, *Anal. Biochem.* 242:84-89; Constans, A, 2003, *The Scientist* 17(13):36; and Bentley et al., 2008, *Nature* 456(7218): 53-59. Other sequencing methods (e.g., sequencing by hybridization) are well known in the art and can be used. Other methods of determining nucleotide sequence can also be used for this invention. For example, sequencing by ligation (e.g., WO1999019341, WO2005082098, WO2006073504 and Shendure et al., 2005, *Science,* 309: 1728-1739.), pyrosequencing (See, e.g., Ronaghi et al., 1996, *Anal. Biochem.* 242:84-89).

14. Compositions and Arrays of DNA Complexes

14.1 DNBs

In one aspect the invention comprises an array of DNA complexes. In one aspect, the array is a support comprising an array of discrete areas, wherein a plurality of the areas comprise (a) single-stranded DNA concatemers, each concatemer comprising a plurality of monomers, each monomer comprising a target sequence and an adaptor sequence;

(b) wherein each of a plurality of monomers of at least a subset of the DNA concatemers in (a) comprise, (i) partially hybridized thereto, a second DNA strand, where each second strand DNA comprises a portion complementary to the target sequence and a portion complementary to at least part of the adaptor sequence, and wherein a portion of the second strand is not hybridized to the concatemer and a portion of the second strand complementary to at least part of the adaptor is hybridized to the adaptor, and (ii) a third DNA strand comprising a portion complementary to, and hybridized to, the target sequence; and (c) wherein each of at least a subset of the plurality of monomers of (b) comprises a fourth DNA strand hybridized to the third DNA strand at a hybridization site, wherein the fourth DNA strand comprises at least a portion of the sequence of the adaptor and the hybridization site is complementary to at least part of the second adaptor sequence.

An array as described above wherein the single-stranded DNA concatemers are immobilized on said discrete spaced apart regions through (i) attractive noncovalent interactions, which may be base-pairing with capture oligonucleotides, or (ii) covalent interactions with discrete spaced apart regions.

It will be appreciated that the DNA complexes of the array may comprise any of the properties of complexes described herein or made according to methods described herein. Additionally the complexes may have any combination of one or more of the following features: (i) the array comprises at least $10^6$ discrete areas, (ii) the concatemers comprise at least 50, more often at least 100, more often at least 500 monomers, (iii) wherein the single stranded DNA concatemers are produced by denaturing a double stranded concatemer in situ, (iv) wherein the fourth DNA strand comprises at least 10 bases of sequence of the adaptor, preferably at least 12 bases, and optionally at least 15 bases, (v) the fourth DNA strand is completely complementary to the second DNA strand to which it is hybridized.

In some embodiments the fourth DNA strand is an oligonucleotide capable of activing as a primer for primer extension (e.g., a sequencing by synthesis reaction), or is an extension product of such a primer, or is an oligonucleotide capable of activing as an anchor for sequencing by ligation, or is an ligation product of such an oligonucleotide and a labeled probe (e.g., a labeled cPAL probe). In one approach the fourth DNA strand comprises a portion complementary to the adaptor sequence and a portion complementary to the target sequence.

14.2 Clusters

In one aspect the invention comprises an array of DNA complexes. In one aspect, the array is a support comprising an array of discrete areas, wherein a plurality of the areas comprise (a) a clonal cluster of double or single-stranded DNAs, each DNA comprising a target sequence flanked by a first adaptor and a second adaptor;

(b) wherein each of a plurality of DNAs of at least a subset of the clusters in (a) comprise, (i) partially hybridized thereto, a second DNA strand, where each second strand DNA comprises a portion complementary to the target sequence and a portion complementary to at least part of first adaptor sequence, and wherein a portion of the second strand complementary to the target sequence is not hybridized to the DNA and a portion of the second strand complementary to at least part of the first adaptor is hybridized to the DNA, and (ii) a third DNA strand comprising a portion complementary to, and hybridized to, the target sequence and a portion complementary to, and hybridized to, the second adaptor sequence; and (c) wherein each of at least a subset of the plurality of DNAs of (b) comprises a fourth DNA strand hybridized to the third DNA strand at a hybridization site, wherein the fourth DNA strand comprises at least a portion of the sequence of the second adaptor and the hybridization site is complementary to at least part of the second adaptor sequence.

It will be appreciated that the DNA complexes of the array may comprise any of the properties of complexes described herein or made according to methods described herein. Additionally the complexes may have any combination of one or more of the following features: (i) the array comprises at least $10^6$ discrete areas, (ii) wherein the DNAs are single stranded (iii) wherein the fourth DNA strand comprises at least 10 bases of sequence of the adaptor, preferably at least 12 bases, and optionally at least 15 bases, (iv) the fourth DNA strand is completely complementary to the second DNA strand to which it is hybridized.

In some embodiments the fourth DNA strand is an oligonucleotide capable of activing as a primer for primer extension (e.g., a sequencing by synthesis reaction), or is an extension product of such a primer, or is an oligonucleotide capable of activing as an anchor for sequencing by ligation, or is an ligation product of such an oligonucleotide and a labeled probe (e.g., a labeled cPAL probe). In one approach the fourth DNA strand comprises a portion complementary to the adaptor sequence and a portion complementary to the target sequence.

14.3 Compositions

In one aspect the invention provides a composition comprising an array as described above in Section 14.1 or 14.2 and an enzyme selected from DNA ligase and DNA polymerase, wherein the DNA polymerase has strand displacement activity. In an embodiment the composition further comprises fluorescently tagged dNTPs (e.g., dNTP analogs) and/or a pool of tagged oligonucleotide probes.

15. Examples

15.1 Example 1: Generation of Complementary Overhangs on DNBs for Paired-End Sequencing In this example, sequencing by synthesis of a known adaptor sequence was carried out using Complete Genomics (CGI's) DNB array chip (DNB Nanoball™ Array). DNBs were produced by rolling circle amplification using a library of single stranded circles comprising human genomic DNA fragments and adaptor Ad 141-2. Ad 141-2 5'-AAGTCGAGGCCAAGCGGTCTTAGGAAGACAAGCTCGAGCTCGAGCGATCGGGCTTCGACTGGAGAC-3' (SEQ ID NO: 1; see FIG. 5). 1 uM extension primer Ad120_3T_21bp: 5'-GAT CGG GCT TCG ACT GGA GAC-3' (SEQ ID NO: 2; "first extension primer") and 1 uM extension primer CX117: 5'-AAG TCG GAG GCC AAG-3' (SEQ ID NO: 3; "second extension primer"), see FIG. 5, were hybridized to an array of DNBs for 30 min. at 35° C. In this experiment primers were selected so that 21 bases of the adaptor sequence was determined (therefore, all of the DNBs in the array give the same sequence read-out).

The primers were then extended (second and third strand synthesis) in an extension mix containing Phi29 polymerase 1.0 U/ul in 1× Phi29 buffer, 0.1 mg/ml BSA, 20% glycerol, 2% DMSO, 25 uM dNTPs to synthesize the complementary strands ("follow-on fragments") for 20 min at 35° C. The extension was then terminated by adding 250 μM ddNTPs.

Sequencing oligonucleotides (4 uM) AD041_Helper or AD041_5T (FIG. 5) were then hybridized to the single-stranded overhang portions of the follow-on fragments (third strands). This was followed by performing SBS for 25 cycles with Cicada at 35° C. with Hot MyChem #2 for 30 min. Reversible Terminator nucleotides (RTs) labeled with 4 different fluorescent dyes were used in the sequencing reaction. TxR stands for Texas Red; FIT stands for Fluorescein; Cy5 stands for Cyanine 5; and Cy3 stands for Cyanine 3. The average of the signal shown in Table 2 represents the average of all the DNBs on the array incorporating a base with the identified base-specific dye. The highest value represents the base that was called for the particular position. For example: in position 1, Cy3 dye associated with base A has is has the highest average of the signal is called A.

Result: All 21 bases are called correctly as the sequenced region is AGA CCG CTT GGC CTC CGA CTT (SEQ ID NO:5), which is the complementary sequence to the adaptor region CX117. Different extension times generated different signal intensities (data not shown). The signals from 21 bases of the complement to the adapter region CX117 were determined. See Table 2.

TABLE 2

Sequencing 21 bases of the complement to the adapter region CX117

| Sequence Position | Average of Mean signal T-TxR | Average of Mean signal C-FIT | Average of Mean signal G-Cy5 | Average of Mean signal A-Cy3 | Base | Sequence |
|---|---|---|---|---|---|---|
|  | 13654.81 | 15846.92 | 11100.77 | 7070.34 |  |  |
| 1 | 6627 | 4146 | 7588 | 31771 | A-Cy3 | A |
| 2 | 3893 | 3935 | 34120 | 4717 | G-Cy5 | G |
| 3 | 5395 | 4362 | 6630 | 23044 | A-Cy3 | A |
| 4 | 5446 | 34991 | 4172 | 5193 | C-A488 | C |
| 5 | 5977 | 40992 | 4549 | 4743 | C-A488 | C |
| 6 | 4095 | 5916 | 31239 | 3959 | G-Cy5 | G |
| 7 | 5836 | 32203 | 4895 | 4406 | C-A488 | C |
| 8 | 43410 | 5268 | 9299 | 4566 | T-TxR | T |
| 9 | 44363 | 4462 | 10226 | 4460 | T-TxR | T |
| 10 | 5752 | 4249 | 25521 | 3842 | G-Cy5 | G |
| 11 | 4469 | 5259 | 19664 | 3845 | G-Cy5 | G |
| 12 | 4917 | 27233 | 4700 | 4240 | C-A488 | C |
| 13 | 7343 | 31210 | 4359 | 4343 | C-A488 | C |
| 14 | 38381 | 7515 | 8589 | 4415 | T-TxR | T |
| 15 | 7325 | 33541 | 4287 | 4457 | C-A488 | C |
| 16 | 6066 | 34245 | 5611 | 4479 | C-A488 | C |
| 17 | 4511 | 6598 | 21302 | 4703 | G-Cy5 | G |
| 18 | 4938 | 6977 | 5693 | 12949 | A-Cy3 | A |
| 19 | 8073 | 27799 | 4444 | 4886 | C-A488 | C |
| 20 | 34835 | 6383 | 8018 | 4601 | T-TxR | T |
| 21 | 35098 | 5501 | 8211 | 4860 | T-TxR | T |
| Grand Total | 13654.8 | 15846.9 | 11100.8 | 7070.34 |  |  |

15.2 Example 2: Sequence Determination of Genomic Sequences

A number of DNBs containing genomic sequences have been sequenced using the invention described herein. The table represents present of the DNBs on the Complete Genomics (CGI's) DNB array chip (DNB Nanoball™ Array) that have been fully uniquely mapped to the genome (labeled as exactly 1 time/0 times or >1 times); L01 & L08: first represent mapping of the first Strand; L02: Adaptor Sequencing (No Genomic Sequencing) and L03-L07: second Strand Genomic Sequencing. The lines L03-L07 have even higher rate of fully uniquely mapped DNBs to the genome (exactly one time). The percent is calculated by using all DNBs arrayed on the array.

TABLE 3

The mapping results of the 25 bases genomic sequence sequenced by SBS

| | # Aligned to Ref | | | | | | | |
|---|---|---|---|---|---|---|---|---|
| | L01 | L02 | L03 | L04 | L05 | L06 | L07 | L08 |
| 0 times | 25.91% | 99.90% | 15.67% | 21.36% | 15.27% | 15.35% | 15.95% | 26.19% |
| exactly 1 time | 54.03% | 0.09% | 63.11% | 58.94% | 63.72% | 63.48% | 62.64% | 53.49% |
| >1 times | 20.06% | 0.01% | 21.22% | 19.71% | 21.01% | 21.17% | 21.41% | 20.33% |

This application is related to U.S. Provisional Application No. 62/117,391, filed Feb. 17, 2015, and incorporated herein by reference in its entirety.

All publications and patent documents cited herein are incorporated herein by reference as if each such publication or document was specifically and individually indicated to be incorporated herein by reference. Although the present invention is described primarily with reference to specific embodiments, it is also envisioned that other embodiments will become apparent to those skilled in the art upon reading the present disclosure, and it is intended that such embodiments be contained within the present inventive methods.

We claim:

1. A method of producing a DNA strand for sequencing, comprising
   a) providing a template DNA polynucleotide strand comprising a first target DNA sequence interposed between a first adaptor 3' to the first target DNA sequence and a second adaptor 5' to the first target DNA sequence, wherein the template DNA polynucleotide strand is immobilized on a substrate and is provided as a first strand,
   b) combining a first primer with the immobilized template DNA polynucleotide strand, and hybridizing the first primer to a first primer binding sequence in the first adaptor, wherein the first primer is not immobilized on the substrate when it is combined with the immobilized template DNA polynucleotide strand;
   c) extending the first primer using one or more DNA polymerases to generate a second strand, wherein the second strand comprises a sequence complementary to the first target DNA sequence and a sequence complementary to at least part of the second adaptor;
   d) combining a second primer with the immobilized template DNA polynucleotide strand, hybridizing a second primer to a second primer binding sequence in the first adaptor, wherein the second primer binding sequence is 3' to the first primer binding sequence, wherein the second primer is not immobilized on the substrate when it is combined with the immobilized template DNA polynucleotide strand; and
   e) extending the second primer using a DNA polymerase having strand-displacement activity to generate a third strand,
   wherein extending the second primer to generate the third strand is carried out under conditions in which the extension of the second primer partially displaces the second strand, thereby producing a partially hybridized second strand having:
   (i) a hybridized portion that is hybridized to the template DNA polynucleotide, and
   (ii) an unhybridized portion that contains a sequence that is complementary to the first target DNA sequence and a sequence that is complementary to at least part of the second adaptor, wherein the unhybridized portion is 5' in the second strand sequence to the hybridized portion.

2. The method of claim 1, further comprising:

f) hybridizing a sequencing oligonucleotide to a sequence in the second or third strand, wherein said sequence is complementary to at least part of the second adaptor, and g) determining at least part of the sequence that is complementary to the first target DNA sequence.

3. The method of claim 1, wherein the first adaptor and the second adaptor have the same nucleotide sequence.

4. The method of claim 1, wherein said one or more DNA polymerases and said DNA polymerase having strand-displacement activity are the same polymerase.

5. The method of claim 1, wherein the second primer binding sequence, to which the second primer is hybridized, is in the first adaptor.

6. The method of claim 1, wherein the template DNA polynucleotide strand comprises a third adaptor and the second primer binding sequence is in the third adaptor.

7. The method of claim 1, wherein the template DNA further comprises a third adaptor 3' to the first adaptor and a second target DNA sequence between the first adaptor and the third adaptor.

8. The method of claim 7, wherein the template DNA polynucleotide strand comprises a DNA concatemer, and wherein the first target DNA sequence and the second target DNA sequence have the same nucleotide sequence.

9. The method of claim 4, wherein the first primer and the second primer are hybridized or extended in the same reaction.

10. The method of claim 1, wherein the template DNA polynucleotide strand comprises a DNA concatemer and the first primer and the second primer have the same nucleotide sequence.

11. The method of claim 8, wherein step d) further comprises hybridizing a plurality of second primers to the plurality of second primer binding sequences, and wherein the plurality of second primers comprise extendable and non-extendable primers.

12. The method of claim 1, wherein extension of the second primer in terminated at a fixed time interval of 5 min, 10 min, 20 min, 30 min, 40 min or 60 min, and wherein extension is terminated by chemical termination and/or addition of ddNTPs.

13. The method of claim 1, wherein the extending the second primer to generate the third strand is controlled by temperature, enzyme concentration, and primer concentration.

14. The method of claim 1, wherein the template DNA polynucleotide strand is deposited on an array, a bead, a well, or a droplet.

15. The method of claim 1, wherein the sequencing is sequencing by synthesis, pyrosequencing, or sequencing by ligation.

16. The method of claim 7, wherein the first adaptor, the second adaptor, and the third adaptor comprise the same nucleotide sequence.

17. The method of claim 7, wherein the template DNA polynucleotide strand is a DNA concatemer comprising multiple copies of a monomer, wherein the monomer comprises one adaptor and one target DNA sequence.

* * * * *